US00PP18597P2

(12) United States Plant Patent
Blom

(10) Patent No.: US PP18,597 P2
(45) Date of Patent: Mar. 11, 2008

(54) ***ECHINACEA* PLANT NAMED 'AVALANCHE'**

(50) Latin Name: *Echinacea purpurea*
Varietal Denomination: Avalanche

(76) Inventor: Arie Blom, Waterbieslaan 110, 3452 AR Vleuten (NL)

( * ) Notice: Subject to any disclaimer, the term of this patent is extended or adjusted under 35 U.S.C. 154(b) by 0 days.

(21) Appl. No.: 11/583,637

(22) Filed: Oct. 19, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Echinacea* plant named 'Avalanche', characterized by its upright, columnar and compact plant habit; moderately vigorous growth habit; freely basal branching habit; and large inflorescences with white-colored ray florets and yellow green-colored disc florets.

2 Drawing Sheets

Botanical designation: *Echinacea purpurea.*
Cultivar denomination: 'Avalanche'.

BACKGROUND OF THE INVENTION

The present invention relates to a new and distinct cultivar of *Echinacea* plant, botanically known as *Echinacea purpurea,* and hereinafter referred to by the name 'Avalanche'.

The new *Echinacea* originated from a cross-pollination in Bovenkarspel, The Netherlands in July, 2003 made by the Inventor of a proprietary selection of *Echinacea purpurea,* identified as code number Ec 202-01, not patented, as the female, or seed, parent with a proprietary selection of *Echinacea purpurea* identified as code number Ec 203-01, not patented, as the male, or pollen, parent. The new *Echinacea* was discovered and selected by the Inventor as a single flowering plant from within the progeny of the stated cross-pollination grown in a controlled environment in IJsselstein, The Netherlands in July, 2004.

Asexual reproduction of the new *Echinacea* by micropropagation a controlled environment in The Netherlands since 2004, has shown that the unique features of this new *Echinacea* are stable and reproduced true to type in successive generations.

SUMMARY OF THE INVENTION

The cultivar Avalanche has not been observed under all possible environmental conditions. The phenotype may vary somewhat with variations in environment such as temperature and light intensity, without, however, any variance in genotype.

The following traits have been repeatedly observed and are determined to be the unique characteristics of 'Avalanche'. These characteristics in combination distinguish 'Avalanche' as a new and distinct cultivar of *Echinacea:*

1. Upright, columnar and compact plant habit.
2. Moderately vigorous growth habit.
3. Freely basal branching habit.
4. Large inflorescences with white-colored ray florets and yellow green-colored disc florets.

Plants of the new *Echinacea* differ from plants of the female parent selection in the following characteristics:

1. Plants of the new *Echinacea* are more compact than plants of the female parent selection.
2. Plants of the new *Echinacea* have not basal branches than plants of the female parent selection.

Plants of the new *Echinacea* differ from plants of the male parent selection in the following characteristics:

1. Plants of the new *Echinacea* are not as compact as plants of the male parent selection.
2. Plants of the new *Echinacea* have larger inflorescences than plants of the male parent selection.

Plants of the new *Echinacea* can be compared to plants of the *Echinacea* cultivar Kim's Mophead, not patented. In side-by-side comparisons conducted in Zuidwolde, The Netherlands, plants of the new *Echinacea* differed from plants of the cultivar Kim's Mophead in the following characteristics:

1. Plants of the new *Echinacea* were more freely branching than plants of the cultivar Kim's Mophead.
2. Ray florets of plants of the new *Echinacea* were more horizontal and less drooping than ray florets of plants of the cultivar Kim's Mophead.

BRIEF DESCRIPTION OF THE PHOTOGRAPHS

The accompanying photographs illustrate the overall appearance of the new *Echinacea.* The photographs show the colors as true as it is reasonably possible to obtain in colored reproductions of this type. Colors in the photographs may differ slightly from the color values cited in the detailed botanical description which accurately describe the colors of the new *Echinacea.*

The photograph on the first sheet comprises a side perspective view of a typical flowering plant of 'Avalanche' grown in a container.

The photograph at the top of the second sheet is a close-up view of a typical inflorescence of 'Avalanche'.

The photograph at the bottom of the second sheet is a close-up view of a typical leaf of 'Avalanche'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Zuidwolde, The Netherlands during the late summer in an outdoor nursery and under conditions and practices which approximate those generally used in commercial *Echinacea* production. During the production of the plants, day temperatures ranged from 12° C. to 30° C. and night temperatures ranged from 4° C. to 15° C. Measurements and numerical values represent averages for typical flowering plants. Plants were about one year old when the photographs and description were taken.

Botanical classification: *Echinacea purpurea* cultivar Avalanche.

Parentage:

*Female parent.*—Proprietary selection of *Echinacea purpurea* identified as code number Ec 202-01, not patented.

*Male parent.*—Proprietary selection of *Echinacea purpurea* identified as code number Ec 203-01, not patented.

Propagation:

*Type.*—By micropropagation.

*Time to initiate roots.*—About one week at 25° C.

*Time to produce a rooted young plant.*—About five weeks at 21° C.

*Root description.*—Fine, fibrous; pale cream white in color.

*Rooting habit.*—Freely branching; moderately dense.

Plant description:

*Plant form/growth habit.*—Upright, columnar and compact plant habit; freely basal branching with about four basal branches developing per plant. Moderately vigorous growth habit.

*Plant height.*—About 40.5 cm.

*Plant diameter or spread.*—About 42.5 cm.

*Basal branches.*—Length: About 26.5 cm. Diameter: About 6 mm. Internode length: About 7.1 cm. Aspect: Mostly upright. Strength: Strong. Texture: Densely pubescent; rough. Color: 144A.

Foliage description:

*Arrangement.*—Alternate, simple.

*Length.*—About 19.4 cm.

*Width.*—About 5.9 cm.

*Shape.*—Narrowly ovate.

*Apex.*—Acute.

*Base.*—Attenuate, elongated.

*Margin.*—Irregularly serrate; undulate.

*Texture, upper and lower surfaces.*—Moderately pubescent; rough.

*Venation pattern.*—Pinnate.

*Color.*—Developing foliage, upper surface: Darker than 143A. Developing foliage, lower surface: 143A. Fully expanded foliage, upper surface: 137A; venation, 145C. Fully expanded foliage, lower surface: 137C to 138A; venation, 145A to 145B.

*Petiole length.*—About 9.4 cm.

*Petiole diameter.*—About 3.5 mm.

*Petiole texture, upper and lower surfaces.*—Smooth, glabrous.

*Petiole color, upper and lower surfaces.*—144B.

Inflorescence description:

*Appearance.*—Rotate single inflorescence form with ray and disc florets. Inflorescences positioned above the foliage on strong peduncles and face upright. About six inflorescences develop per lateral branch. Inflorescences persistent.

*Fragrance.*—Faint; sweet.

*Time to flower.*—Plants flower continuously from late July to late September in The Netherlands.

*Inflorescence longevity.*—Inflorescences maintain good substance for about three weeks on the plant.

*Inflorescence bud.*—Height: About 2.2 cm. Diameter: About 2.5 cm. Shape: Flattened globular. Color: 143A.

*Inflorescence size.*—Diameter: About 8.4 cm. Depth (height): About 3.4 cm. Disc diameter: About 3.5 cm. Receptacle height: About 1.3 cm. Receptacle diameter: About 1.4 cm.

*Ray florets.*—Length: About 3.6 cm. Width: About 8.5 mm. Shape: Narrowly elliptic to narrowly oblanceolate. Apex: Praemorse. Base: Cuneate. Margin: Entire. Texture, upper and lower surfaces: Smooth, glabrous; longitudinally ridged. Number of ray florets per inflorescence: About 20 arranged in a single whorl. Aspect: Horizontal. Color: When opening, upper surface: 157B; towards the apex, 154D. When opening, lower surface: 150D; towards the apex, 145A to 145B. Fully opened, upper surface: 157A to 157B, becoming closer to 155C; towards the apex, 145B; towards the base, 145A. Fully opened, lower surface: 145C; towards the apex, 145B; towards the base, 145A.

*Disc florets.*—Length: About 1 cm. Diameter: About 2 mm. Shape: Tubular, enlarged; apices acute. Number of disc florets per inflorescence: About 500. Texture, upper and lower surfaces: Smooth, glabrous. Color: Immature, inner and outer surfaces: 144B; towards the base, 144D. Mature, inner and outer surfaces: 144B; towards the base, 144D.

*Receptacle spines.*—Quantity: One per disc floret. Shape: Acicular. Apex: Acute. Base: Attenuate. Texture: Smooth, glabrous. Color: Apex: 22A. Midsection: 144A. Base: 145C.

*Involucral bracts.*—Quantity per inflorescence: About 70 in about four whorls. Length: About 8 mm. Width: About 2.5 mm. Shape: Lanceolate. Apex: Acute. Base: Cuneate. Margin: Entire. Texture, upper surface: Smooth, glabrous. Texture, lower surface: Densely pubescent. Color, upper surface: 137A. Color, lower surface: 137A becoming closer to 143A.

*Peduncles.*—Length: Terminal peduncle: About 14.9 cm. Fourth peduncle: About 16.2 cm. Diameter: About 6 mm. Strength: Strong. Aspect: Mostly upright. Texture: Densely pubescent; rough. Color: 144A to 144B.

*Reproductive organs.*—Androecium: (present on disc florets only) Quantity per floret: Five. Filament length: About 4 mm. Filament color: 145D. Anther length: About 2.5 mm. Anther color: 200D. Pollen amount: Moderate. Pollen color: 3A. Gynoecium: (present on disc and ray florets) Quantity per floret: One. Pistil length: About 7 mm. Stigma shape: Cleft; reflexed. Stigma color: 51A. Style length: About 4.5 mm. Style color: 145D. Ovary color: 157D. Fruits/seeds: Fruit and seed development have not been observed.

Disease/pest resistance: Plants of the new *Echinacea* have not been shown to be resistant to pathogens and pests common to *Echinacea*.

Garden performance: Plants of the new Clematis have exhibited good tolerance to rain and wind, have been observed to be hardy to USDA Zone 4 and to tolerate high temperatures of about 35° C.

It is claimed:

1. A new and distinct *Echinacea* plant named 'Avalanche' as illustrated and described.

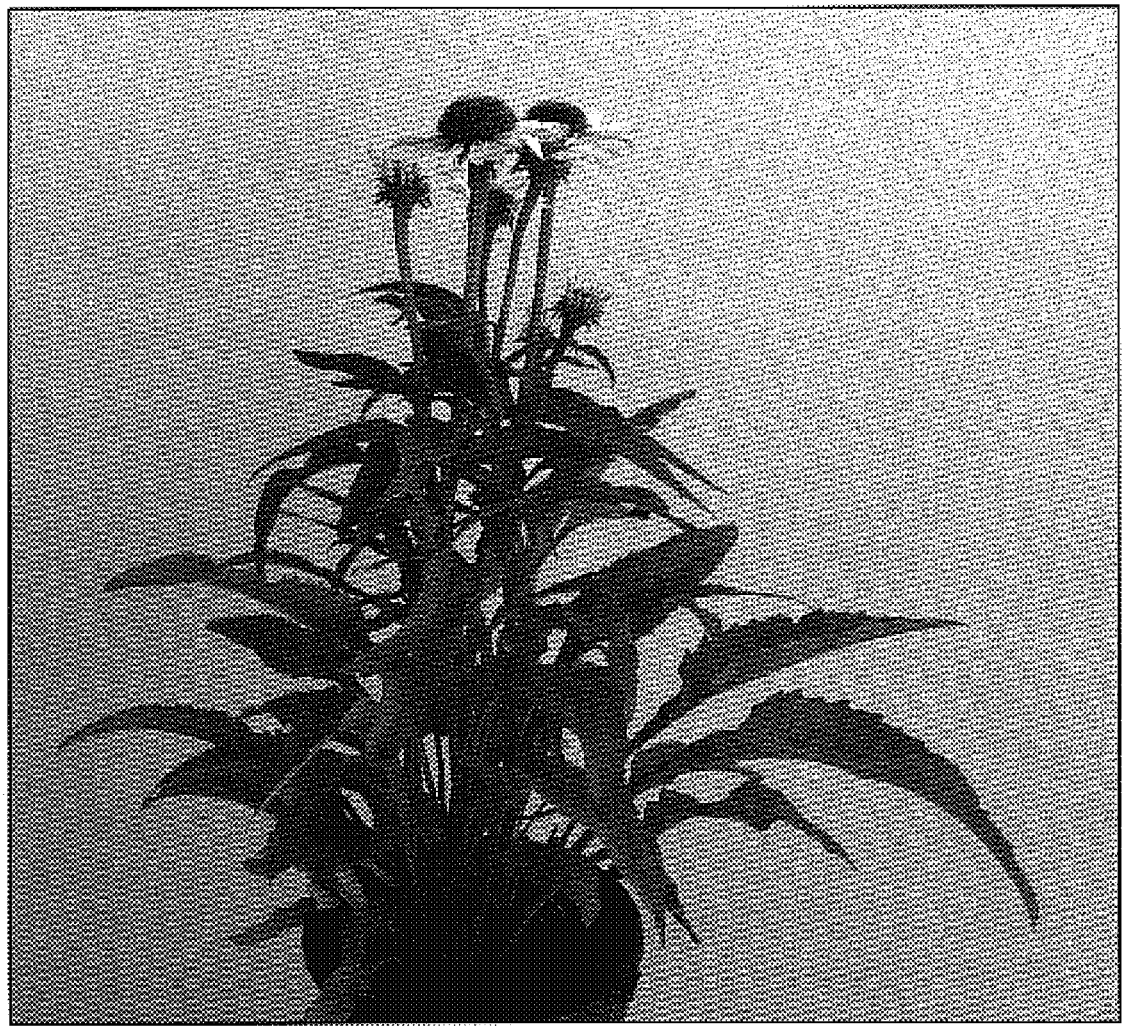

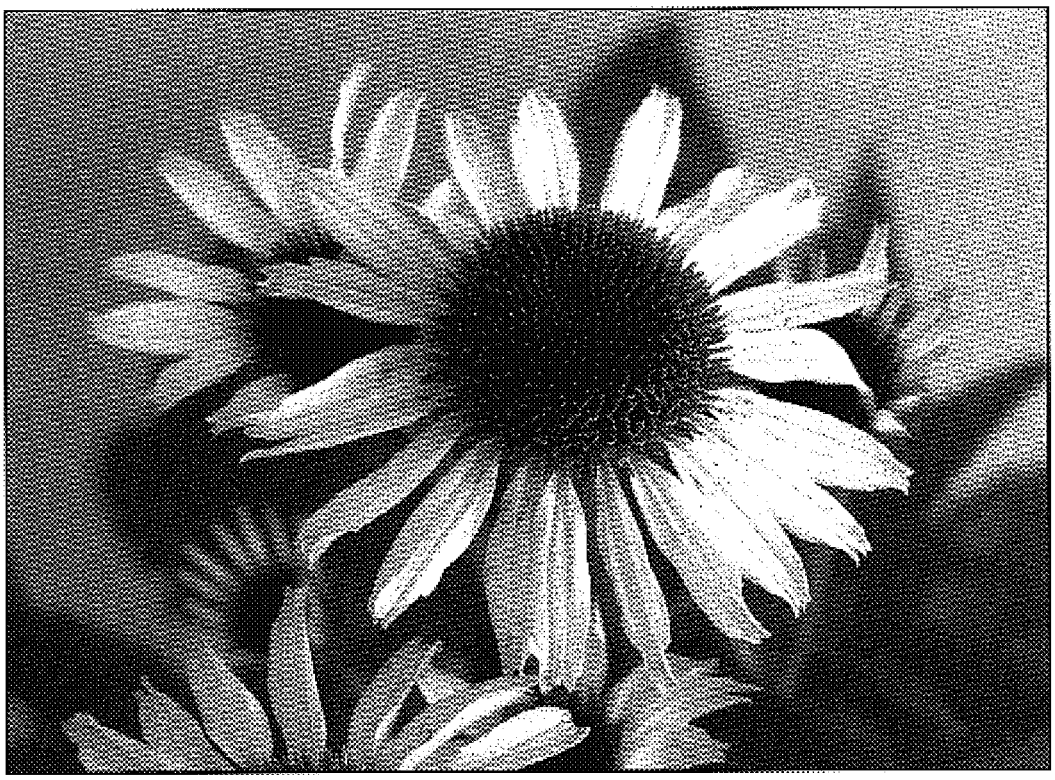
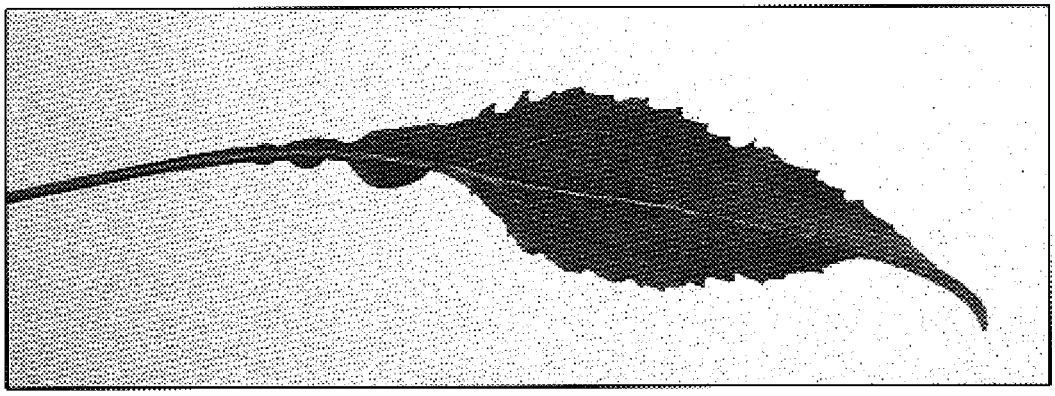

* * * * *